United States Patent
Mata et al.

[11] Patent Number: 6,080,153
[45] Date of Patent: *Jun. 27, 2000

[54] EXTERNAL FIXATION DEVICE

[75] Inventors: Jacques Mata; Marcel Nyfeler, both of Etoy; Denis Worek, Veyrier/GE, all of Switzerland

[73] Assignee: Howmedica International, Ireland

[ * ] Notice: This patent is subject to a terminal disclaimer.

[21] Appl. No.: 09/080,580

[22] Filed: May 18, 1998

Related U.S. Application Data

[63] Continuation of application No. 08/788,718, Jan. 24, 1997, Pat. No. 5,732,954, which is a continuation of application No. 08/520,201, Aug. 28, 1995, abandoned.

[51] Int. Cl.[7] .................................................. A61B 17/56

[52] U.S. Cl. ................................ 606/54; 606/59; 606/61; 606/72

[58] Field of Search ................................. 606/54, 55, 56, 606/57, 58, 59, 61, 62, 72, 73

[56] References Cited

U.S. PATENT DOCUMENTS

| 575,631 | 1/1897 | Brooks . | |
|---|---|---|---|
| 3,154,331 | 10/1964 | Engelhardt | 287/54 |
| 4,700,437 | 10/1987 | Hoshino | 24/456 |
| 5,376,090 | 12/1994 | Pennig | 606/54 |

*Primary Examiner*—Michael Buiz
*Assistant Examiner*—Daphna Shai
*Attorney, Agent, or Firm*—Lerner, David, Littenberg, Krumholz & Mentlik, LLP

[57] ABSTRACT

An articulation element for the relative positioning of fixation bars or bone pins of an external fixator includes a plurality of pairs of jaws. The jaws have on their adjacent faces grooves which form a passage intended to receive a bar or a pin. A spring is interposed between the pairs of jaws. The grooves which form the passage are positioned and arranged so as to have an external opening allowing the bar or bone pin to be snapped in by pressure on it, from the opening of the jaw into the passage, against the spring force which presses the adjacent faces of the haws against one another. This force holds the articulation element on the bars or pins before locking of the articulation by means of a clamping shaft.

15 Claims, 3 Drawing Sheets

Jun. 27, 2000   Sheet 1 of 3   6,080,153

EXTERNAL FIXATION DEVICE

This application is a continuation of corresponding application Ser. No. 08/788,718 filed Jan. 24, 1997, now U.S. Pat. No. 5,732,954 dated May 19, 1998, which is a continuation of Ser. No. 08/520,201, dated Aug. 28, 1995, abandoned.

BACKGROUND OF THE INVENTION

1. Field of the Invention

This invention relates to an external fixation device and more particularly relates to an articulation element for the positioning and the fixation of cylindrical components such as fastening bars, rods or bone pins.

2. Description of the Prior Art

Numerous known external fixators include frames having a specific shape which allow for the location of bone pins to hold the bone fragment into which they are inserted. It is often necessary to insert the pins relatively close to nerves or arteries, which may lead to complications.

For this reason, external fixators have been developed in which the components are assembled after the pins have been inserted into the optimum position with respect to the bone fragment to be held and the tissue surrounding them. The fixation bars or rods making up the frame of the fixator are then placed between the bone pins and articulation elements are used to connect the bars and the pins. It is necessary that these articulation elements allow the bars or pins to be held at variable angulations.

European Patent EP-0,321,472 (WO-88/01152) describes an articulation element for the relative positioning of fixation bars and bone pins of an external fixator. This articulation elements includes a plurality of pairs of jaws having on their adjacent faces grooves which form a passage intended to receive a bar or a pin. Each element includes a locking element for locking the relative angular position of the jaw pairs and a clamping element passing through the pairs of jaws for clamping the bars or pins in a relative position. In addition, each jaw forming a jaw pair is respectively fitted with a positioning projection and a clearance of complementary shape.

One drawback of such a device is that it must be mounted in advance on the fixation bars or the pins which are inserted into the element via their ends. Alternatively, this type of articulation element can be removed before using it and remounted, taking care to arrange the positioning projections and positioning clearances opposite one another. In addition, so long as this device is not locked in the desired final position, the components are not held and can move with respect to one another and, in particular, the articulation element can move freely with respect to the fixation bars and the pins on which it is mounted. However, it is difficult to hold the bars, rods and pins in position before changing especially if several of these types of articulation elements are used. Consequently, it is necessary to hold the articulation element in place before clamping it to the rod or pins.

SUMMARY OF THE INVENTION

The present invention aims to overcome these drawbacks and its subject is an articulation element for the relative positioning of fixation bars or of pins of an external fixator. The articulation element of the present invention includes at least one pair of jaws having grooves on their adjacent faces which grooves form a passage intended to receive the bar or pin. A locking element is provided for locking the relative angular position of the jaws and a clamping element provided which pairs of jaws for clamping the bars or pins held between the jaws in the desired position.

An elastic or spring element is interposed between the pairs of jaws. The grooves forming the passage for the pins are positioned and arranged so as to have an external opening allowing the bar or pin to be snapped in by pressure on the bar or pin in a direction towards the opening of the jaw against the force of the elastic or spring element and into the passage. The elastic element which presses the adjacent faces of the jaws against one another holds the articulation element on the bars or pins before the clamping element is locked.

In the preferred embodiment, the clamping means consists of a shaft which interacts with a stop piece for holding the stack of jaws around the clamping shaft when the latter is unclamped.

The invention also extends to an external fixator including at least one bone pin inserted on either side of the fracture, a frame composed of fixation bars, and at least one articulation element arranged between a pin and a bar or between two bars for their relative positioning. It is characterized in that the articulation element includes in the preferred embodiment, at least two external openings allowing bars or pins to be snapped in by pressure on them into passages provided for this purpose. This pressure acts against the elastic or spring element which holds the bars or pins between the jaws constituting the articulation element.

Using the articulation element of the present invention results in the fixator having the advantage of reduced bulk. In addition, one or more bars can be removed during the bone consolidation.

These and other objects and advantages of the present invention will become apparent from the following description of the accompanying drawings, which disclose several embodiments of the invention. It is to be understood that the drawings are to be used for the purposes of illustration only and not as a definition of the invention.

BRIEF DESCRIPTION OF THE DRAWINGS

In the drawings, wherein similar reference characters denote similar elements throughout the several views.

DESCRIPTION OF THE PREFERRED EMBODIMENT

Figure 1:
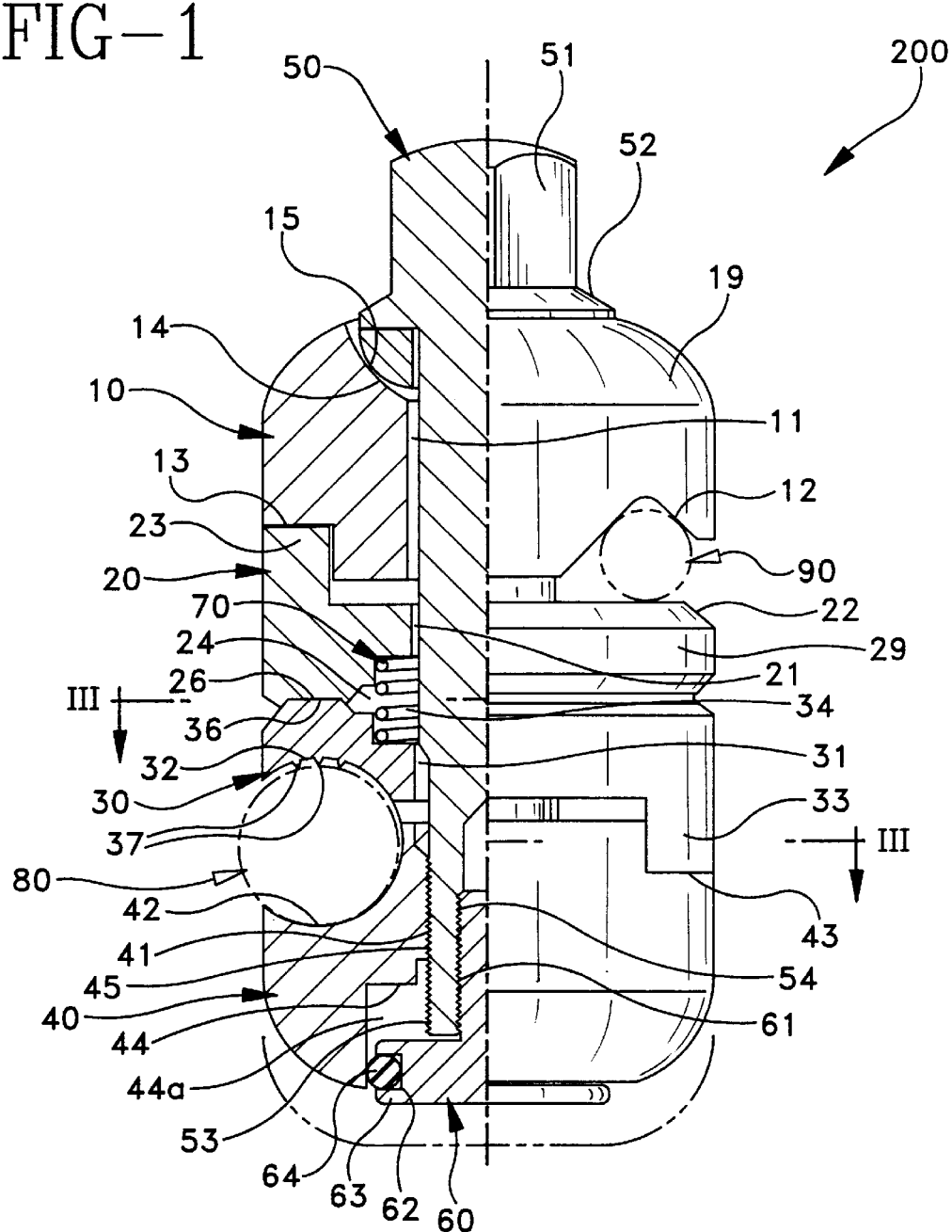
FIG. 1 is a representation of a connector element according to the invention, seen in section in the left part and laterally in the right part of the drawing.

The articulation element generally denoted as 200 is represented in FIG. 1 is composed of a stack of two pairs of jaws, i.e., four jaw members, respectively consisting of an upper jaw 10 and an upper intermediate jaw 20, as well as of a lower intermediate jaw 30 and a lower jaw 40. These four jaws are mounted on a clamping shaft 50 which permanently holds the jaws together by virtue of the stop piece 60. Elastic element 70, such as a spring, is arranged between the intermediate jaws 20 and 30 and tends to separate them i.e., push them apart. A fixation bar 80 and a bone pin 90 have been drawn in phantom in FIG. 1, these being seen in section and arranged parallel on either side of shaft 50 in the example represented.

In the embodiment represented in FIG. 1, the articulation element is shown in the position where the bars or pins are unclamped. When the clamping shaft 50 is unclamped by unscrewing, the lower jaws 30 and 40 are moved, under the action of the elastic element, to the bottom position represented in dashes in the drawing.

The upper jaw 10 includes a central opening 11 for passage of clamping shaft 50. On its face adjacent to intermediate jaw 20 it includes, a notch 12 of a shape corresponding to the part to be clamped and a positioning recess 13 which mate to prevent the relative rotation of the jaw pair 10 and 20. On its opposite face, the upper jaw 10 has a spherical hollow 14 intended to receive a spherical washer 15 arranged around the head of the clamping shaft 50.

The upper intermediate jaw 20 has a central opening 21 for clamping shaft 50. On its face adjacent to the upper jaw, it includes a level 22 for the part to be clamped and an axial projection 23 of a shape corresponding to the positioning recess 13 which mate to prevent the relative rotation of the jaw pair 10 and 20. On its opposite face, jaw 20 includes a recess 24 for the elastic element 70 preferably at the center of the contact surface 26 which contacts with the lower intermediate jaw 30.

Figure 3:
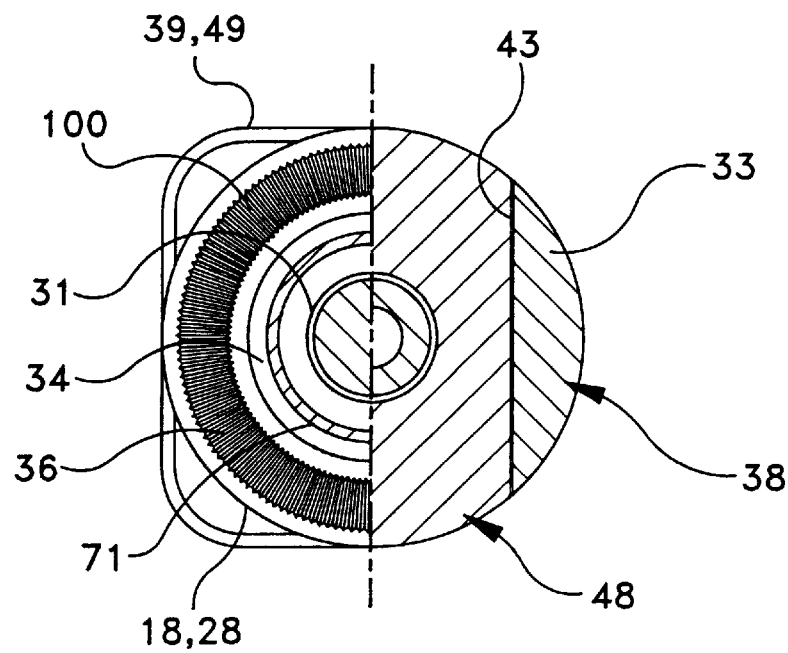
FIG. 3 is a view in cross-section along the line III—III in FIG. 1.

The lower intermediate jaw 30 includes a central opening 31 for shaft 50, a groove 32, an axial projection 33, a central recess 34 and a contact surface 36, which is best shown in FIG. 3. It will be noted that the contract surface 36 may consist of a ring of teeth 100 intended to reinforce the angular locking of the two intermediate jaws 20 and 30. These teeth are relatively fine, in order to allow the intermediate jaws to be locked in a large number of relative positions.

Figure 1A:
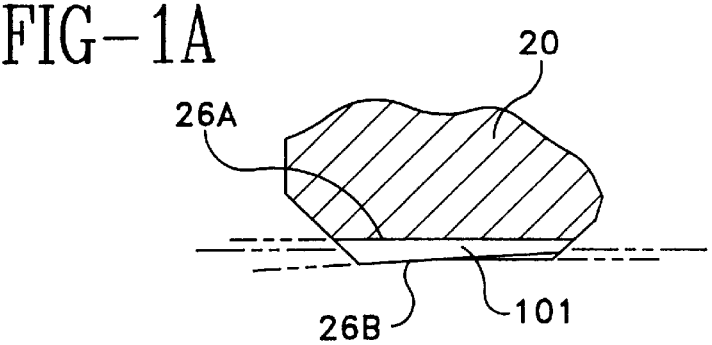
FIG. 1A is an enlarged view of a jaw fragment, showing one embodiment of the means for locking the relative angular position of the pairs of jaws.

In the enlarged view in FIG. 1A, it will be noted that the contract surface 26 of jaw 20 also consists of a radially running teeth 101, of which the bottom 26A is inclined by a few degrees with respect to the horizontal whereas the edge 26B is inclined in the opposite direction, so as to ensure better engagement between the intermediate jaws.

The inner surface of groove 32 includes striations or ridges 37 for ensuring better engagement along the bar 80, as shown in FIG. 1. It is obvious that these longitudinal projections may be replaced by points or friction materials to prevent any relative movement of the components.

The lower jaw 40 is distinguished from those described hereinabove in that the central opening 41 is threaded so as to receive a threaded end 50a of the clamping shaft 50. This lower jaw includes, like the upper jaw 10 already described, a groove 42 for the bar to be positioned, a recess 43 interacting with the projection 33 to prevent relative rotation and a central recess 44 for the stop piece 60. A diagrammatic representation has also been given of a threaded coil sleeve 45 usually of stainless steel, for reinforcing the internal screw thread made in the central opening 41 when the jaw is made of light material such as aluminum.

In the preferred embodiment represented in the drawing, the jaws are formed as a tubular stack. It will be noted in FIGS. 2 and 3 that the preferred jaws have a circular cross-sectional shape 18, 28, 38 and 48 on the side including the positioning projections and the clearances of corresponding shape, whereas they have a square cross-sectional shape 19, 29, 39 and 49 on their parts provided with grooves for receiving the bars, in order to increase their surface area in contract with the bar, rod or pin to be positioned therein.

The clamping shaft 50 includes a head at one end having a square or hexagon shape to receive a tool. In the preferred embodiment it consists of a square head 51 which is flared at its base in order to form a circular shoulder 52 intended to interact with the washer 15. At the other end, the shaft includes a screw thread 53 and a tapped bone 54. Screw thread 53 is intended to interact with threaded opening 41 of the lower jaw or with the threaded coil sleeve 45. Tapped bore 54 receives the stop piece 60.

Figure 2:
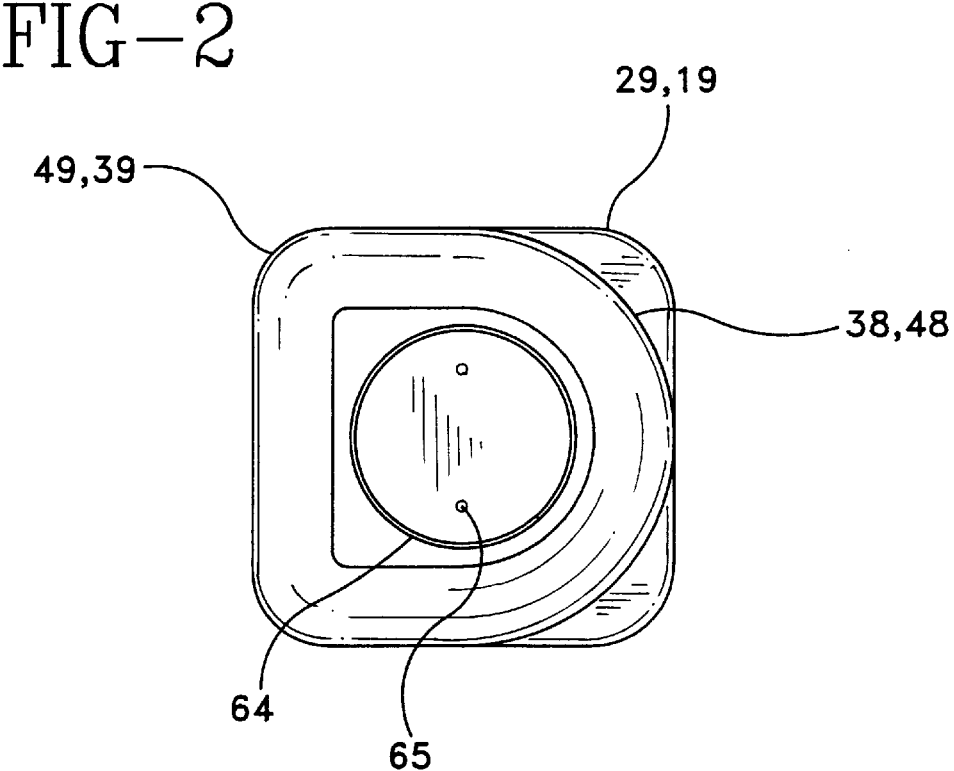
FIG. 2 is a bottom view of the connector in FIG. 1.

Stop piece 60 includes a threaded rod 61 and a closure flange 62, the edge 63 of which includes a channel for accommodating an O-ring seal 64. As seen in FIG. 2, the flange 62 includes two holes 65 intended to receive a tightening spanner when the shaft 50 is screwed into stop piece 60. These two parts will preferably be adhesively bonded so stop 60 will not become uncoupled. Stop piece 60 is used for holding the stack of jaws around the clamping shaft 50 in order to prevent the latter from detaching from the lower jaw.

The elastic element or spring 70 which tends to separate the intermediate jaws 20 and 30 consists, more precisely, of a compression coil spring 70 whose ends bear on the bottom of the recesses 24 and 34. FIG. 1 shows the position of articulation elements when they are clamped onto the cylindrical parts 80 and 90 shown in phantom. The spring 70 is shown as being compressed between the intermediate jaws 20 and 30, whereas FIG. 3 shows one coil turn 71 of the spring 70. When clamping shaft 50 is unclamped with respect to lower jaw 40, this spring 70 tends to separate the pairs of jaws 10, 20, and 30, 40, the flange 62 coming to abut the bottom 44a of the central recess 44. It will further be noted that the height of the projections 23 and 33 is greater than the empty space between the flange 62 and the bottom of the central recess 44, in order to ensure positioning of the pairs of jaws when the articulation element 200 is in the open position.

In the preferred embodiment shown in FIG. 1, a fixation bar 80 and a bone pin 90 have been drawn in phantom, arranged parallel on either side of the shaft 50, but in practice, they are mounted in an arbitrary angular relationship about shaft 50. Conventionally, the fixation bar 80 has a larger diameter than that of the bone pin 90. In this situation the lower jaws 30 and 40 include round grooves 32, 42, the radius of which corresponds to that of the fixation bar 80. The upper jaws 10 and 20 respectively include a V-shaped profiled notch 12 and a level 22 intended to facilitate lateral insertion of bone pin 90. It is also possible to use upper jaws which each include a round groove 32, 42 when the articulation element 200 joins two fixation bars 80, as will be seen hereinbelow.

As already mentioned, the great advantage of the articulation element 200 of the present invention is that it can at all times be arranged on the pins or the bars which can be engaged by a lateral snapping action with the intermediate jaws moving freely against the spring 70. This spring is sufficiently powerful to hold the pins or the bars when snapped in position during reduction and before the practitioner has clamped the shaft 50 by turning head 51 to compress the assembly, which makes it possible to lock the pins or bars as well as the angular position of the intermediate jaws in a single operation.

It will furthermore be noted that, when the shaft 50 is unclamped, it remains held in the lower jaw 40 because of the presence of the stop piece 60 which comes to abut on the bottom of the recess 44. The practitioner is therefore not at risk of accidentally disassembling the components forming the articulation element when the screw 50 is loosened. By way of variant, provision may be made for the clamping shaft 50 to pass freely through the stack of jaws in order to interact with a stop piece allowing the assembly to be locked and unclamped.

Figure 4:
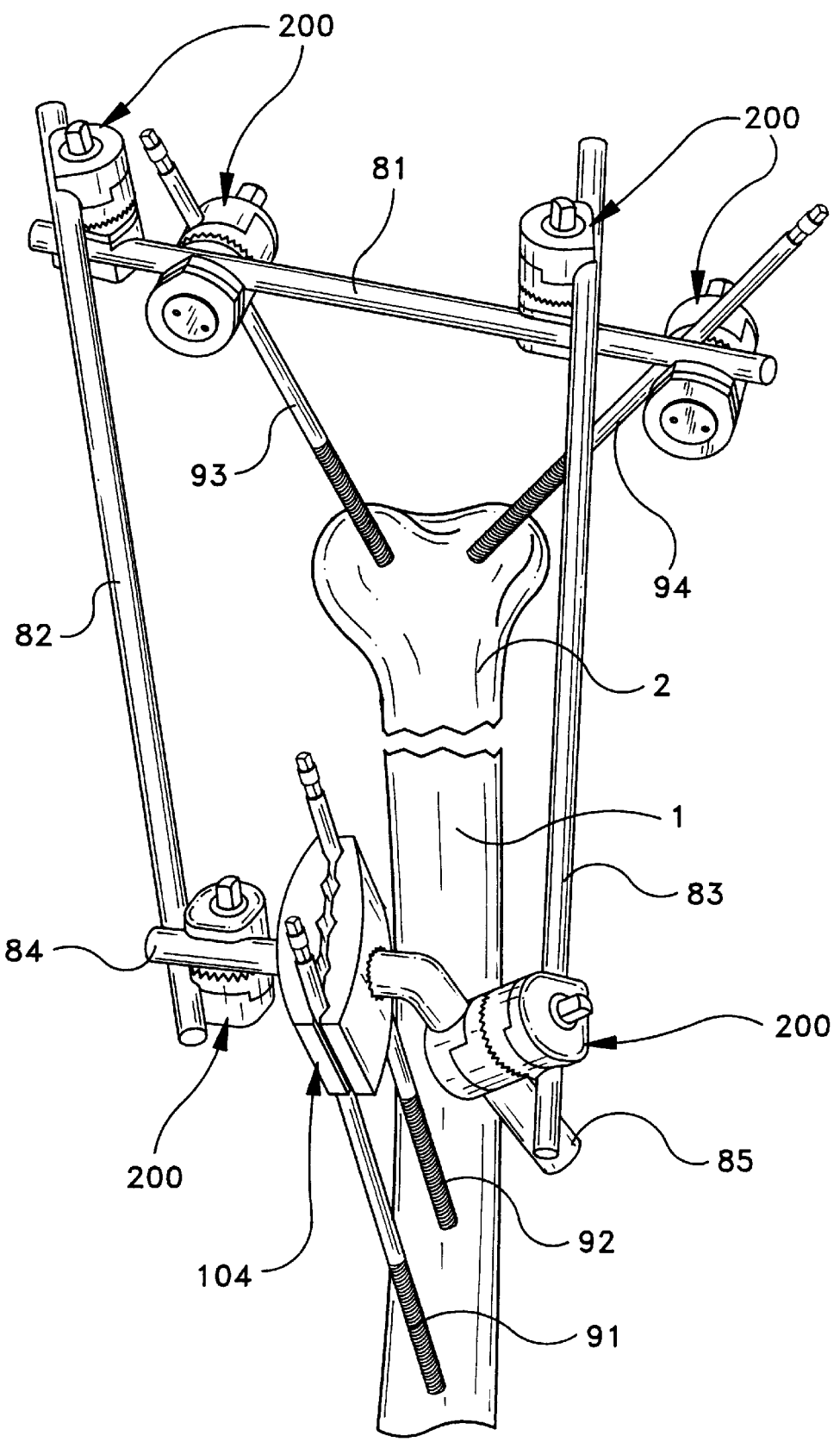
FIG. 4 is a diagrammatic perspective view of a fixator including different variants of connectors according to the invention, mounted on a long bone.

In the example of use represented in FIG. 4, the pins 91 and 92 are inserted into the diaphysis 1 of a bone which is fractured in the vicinity of the epiphysis 2 which receives the pins 93 and 94. Two pins are represented in each bone fragment, but it is obviously possible to insert a larger number of bone pins.

A first fixation bar 81 constitutes the upper part of the frame of the fixator, the bars 82 and 83 of which constitute the sides. The pins 91 and 92 are held in a vice 100 whose jaws receive two bars 84 and 85 which constitute the lower part of the frame of the external fixator.

The articulation element 200 between the pins 93, 94 and the bar 81 are those represented in FIG. 1, whereas all the other articulation elements 200 are arranged between two bars and therefore consist of two pairs of jaws which both include grooves 32, 42 of rounded cross-section.

It should be noted that bent bars may advantageously be employed, such as the bar 84 which has, where it leaves the vice 100, an angle of approximately 135°, or any other value lying between approximately 110° and 160°. This design has the advantage of preventing rotation of the bar in the linkage part when torsional couples are applied to the assembly while at the same time improving the distribution of the forces. In addition, it makes it possible to locate the fixator as close as possible to the fractured limb in order to decrease the bulk of the assembly.

In order to reduce the weight of the fixator, it will be chosen to make certain parts of a light metal alloy such as aluminum or any composite material, for example for the outer jaws 10 and 40. As regards the intermediate jaws 20 and 30, they will preferably me made of steel, in order for the teeth 26 and 36 as well as the ridges 37 not to be deformed.

While several examples of the present invention have been described, it is obvious that many changes and modifications may be made thereunto, without departing from the spirit and scope of the invention.

We claim:

1. An articulation element for the relative positioning of fixation bars, rods or pins of an external fixator, comprising as least one pair of jaws mounted around an internal shaft and arranged along an axis of said shaft and having adjacent faces with at least one face having a groove extending in direction transverse to said axis which groove forms a passage intended to receive said rod, bar or a pin wherein said groove is positioned on said jaw radially outwardly from said internal shaft;

an elastic element acting on at least one of said jaws tending to press said adjacent faces together;

a clamping element for clamping said pair of jaws together and locking said rods, bars or pins held between said jaws in a relative position;

said groove forming said passage is positioned and arranged so as to have an external opening along said transverse direction allowing the bar, rod or pin to be placed in said passage by pressure in a direction perpendicular to both said axis of said shaft and said direction transverse to said axis against the force of said elastic element which presses the adjacent faces against one another to hold the articulation element on the bars, rods or pins before the clamping element locks the pairs of jaws, said passage formed by said groove having a cross-section smaller than a cross-section of said pins rod or bars prior to the rod, bar or pin being placed therein.

2. The articulation element as set forth in claim 1 wherein said elastic element acts in a direction parallel to said shaft.

3. The articulation element according to claim 2, wherein said elastic element consists of a coil spring arranged around a central shaft arranged along said axis.

4. The articulation element according to claim 3, further comprising a stop piece interacting with said central shaft and capable of holding the jaws on said shaft.

5. The articulation element according to claim 1, wherein each of the opposed jaws have a grooved surface.

6. The articulation element according to claim 5, wherein the grooves are of a rounded cross-section.

7. The articulation element according to claim 5, wherein said grooves have projections intended to improve engagement with the bars or pins.

8. The articulation element according to claim 5, wherein said grooves consist of at least two secant plane surfaces.

9. The articulation element according to claim 1, further including a second pair of jaws having intermediate jaw members contacting surfaces and a locking element is provided for locking the relative angular position of the pairs of jaws which consists of said contact surfaces having radial teeth, the bottom surface of which are inclined by a few degrees with respect to a plane perpendicular to the central shaft, whereas the crest is inclined in the opposite direction so as to ensure better engagement between the intermediate jaws.

10. An articulation element for clamping rods or bars of an external fixator comprising:

a shaft;

at least one pair of jaw members mounted on and surrounding said shaft, said jaw members having adjacent faces, at least one jaw member movable with respect to said shaft, at least one of said jaw members having a partial groove formed in the face thereof, said groove partially circumferentially open to an outer surface of said jaw member in a direction transverse to said shaft;

an elastic element engaging said at least one moveable jaw member, forcing the partial circumferential opening of said groove toward the face of said other jaw member, an initial width of said partial circumferential opening of said groove being less than a cross-section of said rod or bar so that the rod or bar may be inserted therein in radial direction with respect to said groove and said shaft against said force of said elastic element; and a locking element engaging said shaft and at least one of said jaw members to lock said jaw members against the bar or rod captured in said groove.

11. The articulation element as set forth in claim 10 wherein said elastic element is a coil spring surrounding said shaft.

12. The articulation element claimed in claim 11 wherein said minimum cross-section of said recess is smaller than a cross-section of said rod or pin.

13. An external fixator for locating at least two bone pins for insertion on either side of a fracture and connected by rods comprising:

at least one articulation element arranged between one of said pins and a rod or between two rods for their relative positioning, said articulation element comprising at least one pair of jaw members mounted on and surrounding a shaft extending along a central axis of said articulation element, at least one jaw member of said pair having an internal transverse recess forming a passageway therethrough for receiving said pins or rod, said passage having an outwardly facing opening for receiving said pin or rod along an axis transverse to said central axis, said opening intersecting with the passageway allowing insertion of said pin or rods in a radial direction with respect to said passageway;

a spring element acting against at least one of said jaw members of said pair of jaw members; and a stop surface formed on said adjacent members to define a minimum cross-section of said recess and a width of said opening, said spring element resisting forces tending to increase with width of said opening generated by the insertion of said pin or rods into said passageway.

14. The external fixator according to claim 13 wherein at least one of said rods is bent along it s length at an angle lying between 110° and 160° to prevent sliding of the rod in the articulation element when it is subjected to torsion and to reduce the bulk of the fixator.

15. The articulation element as set forth in claim 13 wherein said elastic element is a coil spring surrounding said shaft.

* * * * *

UNITED STATES PATENT AND TRADEMARK OFFICE
CERTIFICATE OF CORRECTION

PATENT NO. : 6,080,153
DATED : June 27, 2000
INVENTOR(S) : Mata et al.

It is certified that error appears in the above-identified patent and that said Letters Patent is hereby corrected as shown below:

On the face of the patent:

After "[22] Filed: Feb. 25, 1999" insert the following new line:
-- [30] Foreign Application Priority Data
  Sept. 6, 1994  Switzerland     02 709/94-3 --.

Under "Related U.S. Application Data", line 2, "5,732,954" should read
-- 5,752,954 --.

Column 6, line 59, "11" should read -- 13 --.

Signed and Sealed this

First Day of May, 2001

*Attest:*

NICHOLAS P. GODICI

*Attesting Officer*    *Acting Director of the United States Patent and Trademark Office*